United States Patent [19]

France

[11] Patent Number: 5,599,275
[45] Date of Patent: Feb. 4, 1997

[54] APPARATUS FOR STRETCHING A PENIS

[76] Inventor: Daniel R. France, Road 2, Box 8061 D, Milford, Pa. 18337

[21] Appl. No.: 336,670

[22] Filed: Nov. 7, 1994

[51] Int. Cl.⁶ ..................................................... A61F 5/00
[52] U.S. Cl. ............................................................. 600/38
[58] Field of Search ................ 600/38–41; 128/897–98; 482/93, 99, 105; 33/392

[56] References Cited

U.S. PATENT DOCUMENTS

| 1,073,525 | 9/1913 | Russell. |
| 1,095,899 | 5/1914 | Macarthy. |
| 4,203,432 | 12/1978 | Koch. |
| 4,834,115 | 6/1987 | Stewart. |

FOREIGN PATENT DOCUMENTS

| 427488 | 3/1926 | Germany. |
| 440947 | 2/1927 | Germany. |
| 2652353 | 3/1978 | Germany. |

Primary Examiner—Angela D. Sykes
Assistant Examiner—John P. Lacyk
Attorney, Agent, or Firm—Hoffman, Wasson & Gitler, P.C.

[57] ABSTRACT

A device for lengthening a penis is provided having two semicircular parts connected by a hinge so that the semicircular parts can be opened and closed, and so that the device is adjustable to a variety of widths. A retaining ring is provided to maintain the semicircular parts in a closed position. The semicircular parts fit around the penis and are weighted to lengthen the penis over time.

10 Claims, 1 Drawing Sheet

APPARATUS FOR STRETCHING A PENIS

BACKGROUND OF THE INVENTION

1. Field of the Invention

The present invention relates to an apparatus for stretching of human tissue, and in particular the glans penis. The present invention utilizes weights to accomplish stretching of the penis.

2. Description of the Prior Art

A significant percentage of the male population is dissatisfied with the length of their penis. The length of a man's penis is given considerable significance relative to his ability to satisfy his partner during intercourse. Men with shorter than average penises are subject to ridicule and a corresponding amount of self-doubt and lack of confidence.

Recently, methods have been developed to enlarge the penis. These methods, however, are surgical in nature, usually requiring the injection of fat from another part of the body. Such procedures run the same risks attendant to all surgery, infection, complications, and adverse reactions to drugs used during the procedure, to name a few. Furthermore, such procedure, if effective at all, are better at increasing the circumference of the penis as opposed to the length. In addition, the degree of permanance of any change is doubtful.

SUMMARY OF THE INVENTION

These and other deficiencies of the prior art are addressed by the present invention which is directed to an apparatus for stretching human tissue of the male gender, and specifically the glans penis. The apparatus is a circular weight that is fitted to the penis to effectuate permanent elongation of the penis.

An object of the present invention is to provide an apparatus for effectuating permanent elongation of the penis.

Another object of the present invention is to provide an apparatus for effectuating permanent elongation of the penis that can be worn under normal clothing and not be noticable to others.

Yet another object of the present invention is to provide a device for elongating a penis which is non-irritating and does not cause allergic reactions.

Still another object of the present invention is to provide a device for elongating a penis which does not require an invasive procedure such as surgery.

Another object of the present invention is to provide a device for elongating a penis which allows urination while it is being worn.

BRIEF DESCRIPTION OF TEE DRAWINGS

These and other attributes of the present invention will be described with respect to the following drawings in which.

DETAILED DESCRIPTION OF THE INVENTION

Figure 1:
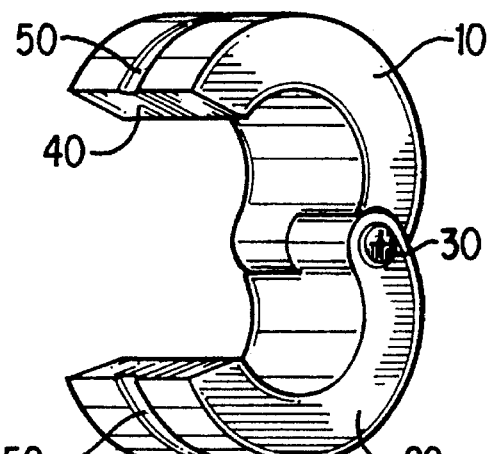
FIG. 1 is a perspective view of an apparatus according to the present invention.
Figure 2:
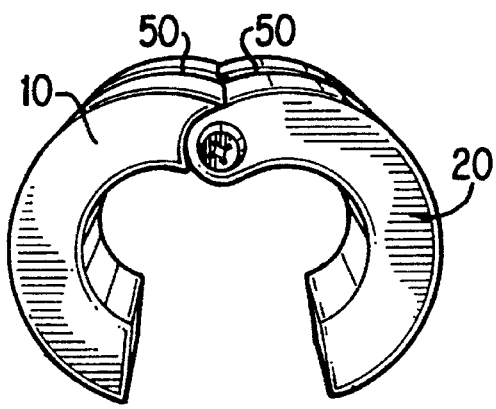
FIG. 2 is a perspective view of an apparatus according to the preset invention in the open position with the opening facing downward.
Figure 3:
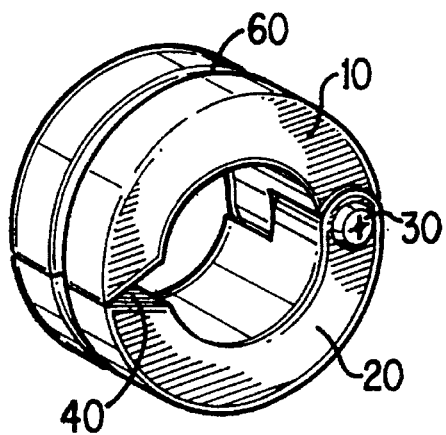
FIG. 3 is a perspective view of an apparatus according to the present invention in the closed position.

Referring to FIGS. 1–3, the present invention is formed from two semicircular parts 10 and 20, which are joined by a hinge 30 so that they form a complete circle in the closed position. Semicircular parts 10 and 20 can opened to fit the device around a penis, and the hinge 30 allows the parts 10 and 20 to be closed about the circumference of the penis. The inner diameter of parts 10 and 20 are chosen so that the device will fit penises of various diameters.

The faces 40 of each semicircular part 10 and 20 is beveled to form a "V" when in the closed position. The "V" permits the wear to urinate while wearing the device, without experiencing discomfort.

A groove 50 is provided in the outercircumference of each of the parts 10 and 20 to accomodate a retaining ring 60. The retaining ring 60 can be stainless steel or a rubber band. The ring 60 holds the the parts 10 and 20 of the device securely closed while also allowing the penis room to expand and become flaccid without losing sufficient fit or creating discomfort. The surfaces or parts 10 and 20 are formed smooth enough to prevent irritation.

The hinge 30 is a stainless steel screw in the illustrated embodiment, and the semicircular parts 10 and 20 are composed of non-toxic metals, and such as 92% pure tin, 7.75% antimony and 0.25% copper. In the preferred embodiment the parts are 94% pure tin and 6% silver. Such materials minimize the risk of allergic reactions. The metals used should be base metals which are electroplated with a noble metal such as gold, silver, rhodium or platinum. Alternatively, the device can incorporate plastic, such a coating on the semicircular parts 10 and 20.

The device is designed to weigh approximately between 10 and 16 oz. and preferrable is 10 oz. The device can, however be heavier or lighter, and the foregoing range is not meant to be a set limit.

Testing of the device over the course of one year resulted in an elongation of the penis of one inch, where the device was worn for eight hours per day. The device was removed at night.

Having described the preferred embodiment of the apparatus in accordance with the present invention, it is believed that other modifications, variations and changes will be suggested to those skilled in the art in view of the description set forth above, such as varrying the materials from which it is made, as well as the dimensions. It is therefor to be understood that all such variations, modifications and changes are believed to fall within the scope of the invention as defined in the appended claims.

What is claimed is:

1. A device for lengthening the penis comprising:

two semicircular parts connected by a hinge so that said semicircular parts are opened and closed, so that the device is adjustable to a variety of widths; and means for retaining said semicircular parts in a closed position, wherein said semicircular parts fit around said penis and are weighted to lengthen said penis over time, further comprising a groove formed in the outer circumference of said semicircular parts, for accommodating said retaining means.

2. A device as recited in claim 1, wherein said retaining means is a rubber band.

3. A device as recited in claim 1, wherein said retaining means is metal ring.

4. A device as recited in claim 1, wherein said retaining means permits said semicircular parts to move relative to one another about said hinge to accommodate an expanded and flaccid penis.

5. A device for lengthening the penis comprising:

two semicircular parts connected by a hinge so that said semicircular parts are opened and closed, and so that device is adjustable to a variety of widths; and means for retaining said semicircular parts in a closed position, wherein said semicircular parts fit around said penis and are weighted to lengthen said penis over time, wherein said semicircular parts are encased in plastic material.

6. A method of lengthening a penis comprising the steps of:

opening a device having a pair of semicircular parts connected by a hinge;

placing the opened device around said penis toward the distal end of said penis;

closing said device so that said penis is encircled by said device;

attaching a retaining means around an outer circumference of said device to maintain said device in a closed condition.

7. A method as recited in claim 6, further comprising the step of fitting said retaining means into a groove formed in the outer circumference of said device to maintain said device in a closed condition.

8. A method as recited in claim 6, wherein said semicircular parts and said retaining means are selected so as to accommodate an erect and flaccid penis.

9. A method as recited in claim 6, further comprising the step of providing bevelled faces on ends of said two semicircular parts permitting a person wearing said device to urinate while said device is in place.

10. A method as recited in claim 6, further comprising the step of selecting said device so that it has a desired weight to achieve elongation of said penis with prolonged wearing of said device.

* * * * *